United States Patent
D'Angelico et al.

(10) Patent No.: US 7,436,100 B2
(45) Date of Patent: Oct. 14, 2008

(54) DEVICE FOR MONITORING A PREDETERMINED FILLING LEVEL OF A MEASURING MEDIUM IN A CONTAINER

(75) Inventors: Sascha D'Angelico, Efringen Kirchen (DE); Alexander Mueller, Jechtingen (DE)

(73) Assignee: Endress + Hauser GmbH + Co. KG, Hauptstrasse, Maulburg (DE)

( * ) Notice: Subject to any disclaimer, the term of this patent is extended or adjusted under 35 U.S.C. 154(b) by 366 days.

(21) Appl. No.: 10/524,538

(22) PCT Filed: Jul. 18, 2003

(86) PCT No.: PCT/EP03/07841
§ 371 (c)(1),
(2), (4) Date: Oct. 11, 2005

(87) PCT Pub. No.: WO2004/018974
PCT Pub. Date: Mar. 4, 2004

(65) Prior Publication Data
US 2006/0131994 A1 Jun. 22, 2006

(30) Foreign Application Priority Data
Aug. 14, 2002 (DE) ................. 102 37 931

(51) Int. Cl.
*H01L 41/04* (2006.01)
*H01L 41/08* (2006.01)
(52) U.S. Cl. ................... 310/319; 310/316.03
(58) Field of Classification Search ........... 310/311, 310/316–319
See application file for complete search history.

(56) References Cited

U.S. PATENT DOCUMENTS 5,533,381 A * 7/1996 Seale ............... 73/19.03
2005/0140522 A1 * 6/2005 Heilig et al. ........... 340/870.01

* cited by examiner

*Primary Examiner*—Jaydi A San Martin
(74) *Attorney, Agent, or Firm*—Bacon & Thomas, PLLC

(57) ABSTRACT

A vibration detector for determining and/or monitoring a predetermined fill level in a container. The detector includes an oscillatable unit, a driver/receiver unit and an evaluation unit. The vibration detector can, additionally, be used as a viscosity sensor or as a density sensor. For providing a multivariable sensor, a microprocessor is provided in the oscillation circuit formed of oscillatable unit and feedback electronics. The microprocessor corrects the phase of the feedback electronics over a predetermined frequency bandwidth in such a way that the sum of the phases of the feedback electronics and the microprocessor follows a predetermined function f(v).

11 Claims, 1 Drawing Sheet

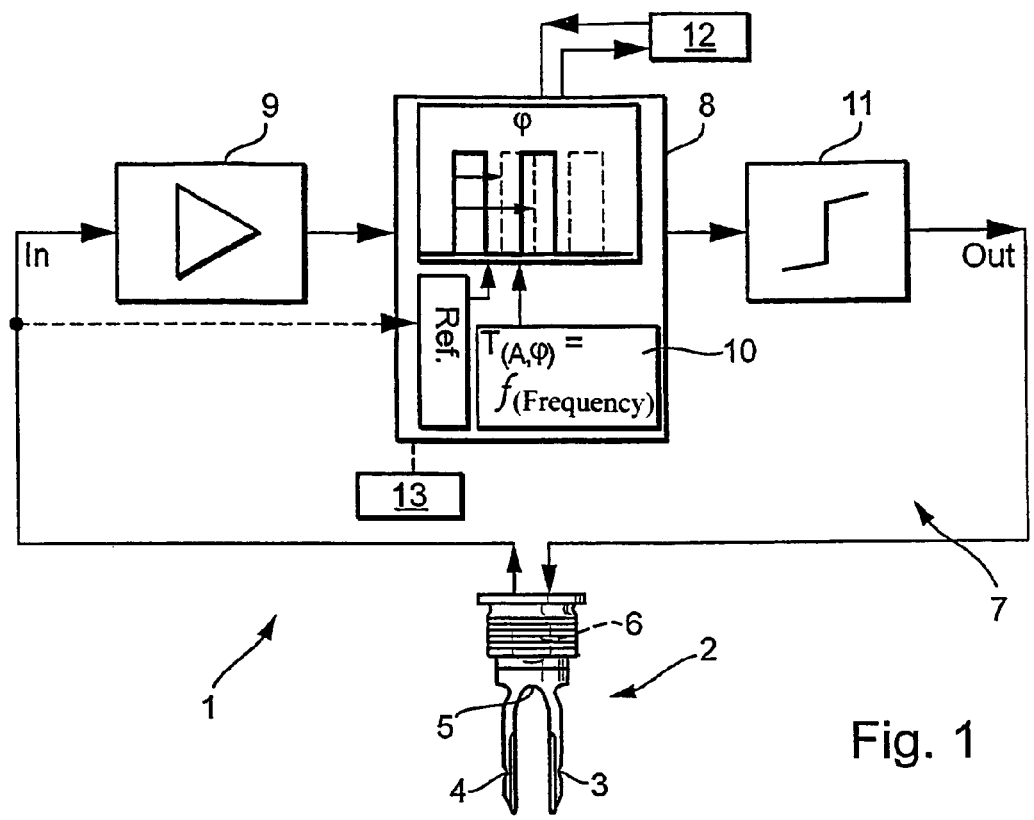
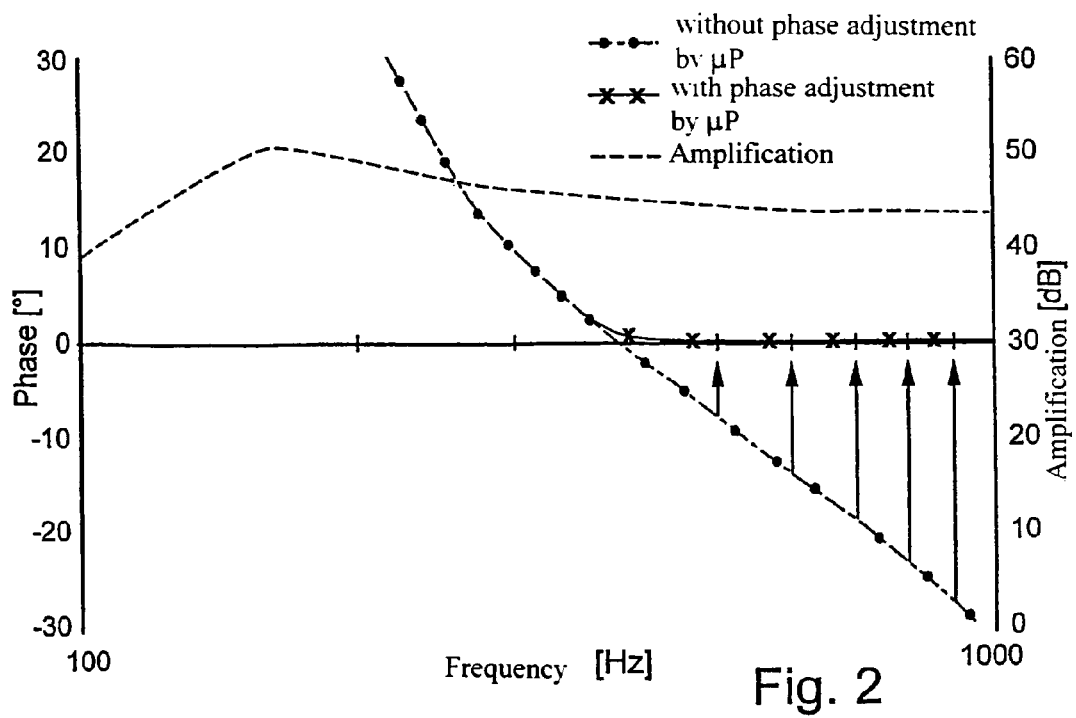
Fig. 1
Fig. 2

DEVICE FOR MONITORING A PREDETERMINED FILLING LEVEL OF A MEASURING MEDIUM IN A CONTAINER

FIELD OF THE INVENTION

The invention relates to an apparatus for monitoring a predetermined fill level of a medium in a container. The apparatus may also be used for determining density or viscosity of a medium in a container. The medium to be measured can be a fluid medium, a foam, or a solid medium.

BACKGROUND OF THE INVENTION

The apparatus includes an oscillatable unit, a driver/receiver unit, and an evaluation unit. The oscillatable unit is, depending on application, placed at the height of the predetermined fill level, or it is positioned such that it reaches to a defined immersion depth into the medium being measured. Additionally, a feedback electronics is provided, which delivers to the driver/receiver unit the signals for exciting the oscillatable unit. The feedback electronics is preferably a fundamental wave exciter, such as is already known from the state of the art. Especially to be referenced here is the fundamental wave excitement used in LIQUIPHANT M. On the basis of a frequency and/or amplitude change of the oscillation of the oscillatable unit, the evaluation unit determines the reaching of the predetermined fill level. In the case of a density or viscosity measurement, the evaluation unit determines the density, respectively the viscosity, of the medium to be measured, as a function of a change of the oscillation of the oscillatable unit.

Apparatuses, so-called vibration detectors, are already known, which employ an oscillatable unit for detecting, respectively monitoring, the fill level of a medium in a container. As regards the oscillatable unit, such is usually at least one oscillation tine, which is secured to a membrane, or diaphragm. The membrane is excited to oscillate via an electromechanical transducer, e.g. a piezoelectric element. The oscillation of the membrane, in turn, causes the oscillatable unit secured to the membrane to oscillate. Vibration detectors of this kind are made and sold by the assignee under the mark 'LIQUIPHANT'.

Vibration detectors in the form of fill level measuring devices make use of the effect that the oscillation frequency and oscillation amplitude depend on the particular amount of covering of the oscillatable unit: While the oscillatable unit executes its (resonance) oscillations in air free and undamped, it undergoes a frequency and amplitude change, thus a detuning, as soon as it becomes immersed, partially or completely, in the medium being measured. On the basis of a predetermined frequency change (usually, for ascertaining fill level, frequency is detected), an unequivocal conclusion can be made concerning the reaching of the predetermined fill level by the medium in the container. Fill level measuring devices are used principally as protection against overfilling or as protection against pumps running empty.

Moreover, the frequency of the oscillation of the oscillatable unit is also influenced by the density of the medium. Consequently, at constant degree of covering, there is functional relationship between frequency change and the density of the medium, so that vibration detectors are well suited both for fill level and for density determination.

In practice, for the purpose of monitoring and detecting the fill level and/or the density or viscosity of the medium in the container, the oscillations of the membrane are registered and converted by means of a piezoelectric element into electrical response signals. The electrical response signals are subsequently evaluated by an evaluation unit. In the case of fill level determination, the evaluation unit monitors the oscillation frequency and/or the oscillation amplitude of the oscillatable unit and signalizes the state 'sensor covered', or the state 'sensor uncovered', as soon as the measured value subceeds, or falls below, on the one hand, or exceeds, on the other hand, a predetermined reference value. A corresponding report to the operating personnel can occur optically and/or acoustically. Alternatively, or additionally, a switching is initiated; for instance, the switching could effect the opening or closing of an inlet or outlet valve on the container.

Moreover, WO 02/31471 A2 discloses an apparatus for measuring and/or monitoring the viscosity of a medium to be measured. The apparatus, also in this case, includes an oscillatable unit secured on a membrane, an driver/receiver unit, and a control/evaluation unit. The control/evaluation unit determines on the basis of the frequency-phase curve the viscosity of the medium being measured. Especially, the control/evaluation unit adjusts to two phase values sufficiently different from one another, determines the frequencies associated with the phases, or the corresponding frequency change of the oscillations of the oscillatable unit, compares the determined frequency change with stored calibration data, and so determines the viscosity of the medium being measured.

SUMMARY OF THE INVENTION

An object of the invention is to provide an apparatus for fill level and/or density or viscosity measurement, which exhibits a constant phase-frequency characteristic over a large frequency bandwidth (working range).

The object is achieved by providing a microprocessor in the oscillation circuit formed of the oscillatable unit and the feedback electronics, with the microprocessor correcting the phase of the feedback electronics over a predetermined frequency bandwidth in such a way that the sum of the phases of the feedback electronics and of the microprocessor follows a predetermined function f(v). The feedback electronics is e.g. an analog feedback electronics, such as that used in the LIQUIPHANT M switch available from the assignee. The invention is, however, not limited to this particular form of feedback electronics.

By the integration, in accordance with the invention, of the microprocessor into the oscillation circuit, it is possible to influence a vibration detector in an 'intelligent' manner such that it exhibits a constant phase-frequency characteristic over an extended working range. Additionally, the detector becomes adjustable for the most varied of conditions and requirements at the measurement site. Moreover, the apparatus of the invention, as a so-called multivariable sensor, can be used both for determining fill level and for measurement of viscosity or density.

In an advantageous further development of the device of the invention, the frequency bandwidth preferably extends between the limits of 300 and 1500 Hz.

The feedback electronics has, furthermore, the task—in case the driver/receiver unit fails—of producing a signalizing by means of the resonance frequency of the feedback electronics (see the amplitude behavior in FIG. 2). This frequency lies outside of the frequency bandwidth of the multivariable sensor.

An advantageous embodiment of the apparatus of the invention provides that a memory unit is associated with the microprocessor and correction values for the phase are stored in the memory unit as a function of the frequency of the oscillation. Especially, the correction values for the phase are accessible in the memory unit in the form of a table or in the form of one or more functions. The latter case occurs, when additional process variables, which influence the phase-frequency characteristic of the feedback electronics, e.g. temperature at the location of measurement, are taken into consideration.

In order to assure an optimal operation of the apparatus of the invention, the microprocessor assures, for example, that the function f(v) assumes a constant value over the entire working range. The constant value can be, for example, 0°. Depending on the application, the sum of the phases of feedback electronics and microprocessor can, however, also exhibit a constant value different from zero. In principle, the constant, which represents the sum of the phases, can assume any value between −180° and +180°. By this embodiment, it is, for example, possible, to react to conditions changed by foam at the measuring site. Equally is it possible to distinguish the foam from the liquid medium being measured, given certain prerequisites. Additionally, a freely changeable phase is—as already mentioned above—an indispensable precondition for the measurement of viscosity.

Consider the following example: A limit value switch is installed as an overfill safeguard in a container, in which a liquid, strongly foaming, measurement medium is stored. In such a case, the limit switch must issue a switching signal as soon as the foam comes in contact with the oscillatable unit and not only after the oscillatable unit reaches into the liquid medium. In order to assure a reaction of the limit sensor to the foam, the sum of the phases of the feedback electronics and the microprocessor is set to a value different from zero, e.g. to +50°. Furthermore, an optimized adjustment for the case that the limit value switch is installed as a run-dry protection can utilize a sum set e.g. to −20°. In such a case, the switching point of the limit switch is set such that the foam is ignored.

According to an advantageous further development of the apparatus of the invention, an input/display unit is provided, on which the function f(v) can be pre-set. In this way, it is possible to choose, depending on application, a density, viscosity or foam measurement, without having to make any hardware changes in the individual components of the electronics part. It is to be noted that data communication can occur without the necessity of on-site input, for example over a field bus.

Preferably, the feedback electronics provides the microprocessor with a periodic, preferably rectangular signal, which is used by the microprocessor for determining a correction value for the phase. In this way, it is achieved that the signal coming from the microprocessor does not have to be converted A/D and filtered in the frequency domain. Instead, the signal coming from the microprocessor can be processed in the time domain. For this reason, a more cost-favorable microprocessor can be used, since no A/D conversion with a computationally intensive filtering in the frequency domain is needed.

Especially, the microprocessor executes the following steps: In a first step, the microprocessor determines on the basis of the edges, e.g. on the basis of the rising edges, of the rectangular input signal, the frequency of the oscillation circuit; subsequently, the microprocessor matches the determined frequency with the corresponding, stored, correction value for the phase; in a third step, the microprocessor arranges for the output of an output signal with the phase corrected as determined in step two. In this way, a regulating of the oscillating circuit to the predeterminable, or predetermined, phase-frequency characteristic is obtained essentially in real time.

Additionally, it is provided that the microprocessor determines the frequency over plural periods of the input signal, and conducts a frequency weighting. It is found in practice that the microprocessor, depending on the quality of the signal, does not always determine the same frequency over a plurality of periods. At this point, a frequency weighting is initiated. Should it for application technical reasons be reasonable to force the oscillatable unit to lower frequencies, then the microprocessor can output the lowest of the frequencies measured in the last periods. Of course, also other application technical factors can be taken into consideration by corresponding presetting of the microprocessor. For instance, a frequency averaging can be performed over plural periods, or the largest determined frequency is selected and fed to the booster mentioned below, for the amplification.

In an advantageous further development of the apparatus of the invention, an amplifier circuit (→booster) is provided, via which the output signals of the microprocessor are fed to the driver unit for the oscillatable unit.

A preferred embodiment of the apparatus of the invention provides that the microprocessor additionally assumes the tasks of the evaluation unit and determines the reaching of the predetermined fill level or determines and signalizes the viscosity, the density or the foam formation of the medium being measured.

An advantageous further development of the apparatus of the invention provides that the feedback electronics provides the microprocessor with a signal which is amplitude-proportional to the input signal. This embodiment is important, when the medium being measured is a solid medium. Thus, e.g., in the case of the SOLIPHANT switch available from the assignee, the amplitude change, and not the frequency change, is evaluated for the purpose of detecting and/or monitoring the fill level.

In addition, a sensor for the measurement of a process variable, e.g. a temperature sensor, is provided, which supplies the microprocessor with information regarding the process variable, e.g. regarding temperature, and the microprocessor considers the influence of the process variable in the providing of the correction value for the phase.

BRIEF DESCRIPTION OF THE DRAWINGS

The invention will now be explained in further detail on the basis of the drawings, the figures of which show as follows:

FIG. 1 is a block diagram of an apparatus of the invention, and

FIG. 2 is a graphic presentation of phase, corrected phase, and amplification plotted against frequency.

DESCRIPTION OF THE PREFERRED EMBODIMENT

FIG. 1 is a block diagram of the apparatus of the invention in the form of a limit switch. The apparatus 1 shown in FIG. 1 is also, as already indicated above, suitable for determining the density or viscosity of a medium in a container. Container and medium are not shown in FIG. 1. While, in the case of fill level determination, the oscillatable unit 2 only reaches into, or leaves, the medium being measured upon arrival of the detected limit fill level, it must be continuously in contact with the medium up to a predetermined immersion depth for the monitoring, or determining, of density or viscosity. As regards the container, it can, of course, also be a pipe containing the medium flowing therein.

The sensor has a housing, which is sealed at its end region protruding into the container by the membrane 5. Membrane 5 is held at the area of its edge in the housing. The oscillatable unit 2 extending into the container is secured to the membrane 5. In the illustrated case, the oscillatable unit 2 is provided in the form of a tuning fork, thus comprising two mutually separated oscillation tines 3, 4 secured to the membrane 5 and extending into the container.

The membrane 5 is caused by the driver/receiver unit 6 to oscillate at a predetermined excitation frequency. The driver/receiver unit 6 is e.g. a stack drive or a bimorph drive. Both kinds of piezoelectric drives are sufficiently known in the state of the art, that a description of them does not need to be given here. Due to the oscillations of the membrane 5, also the oscillatable element 2 executes oscillations, with the oscillation frequency being different, depending on whether the oscillatable unit 2 is in contact with the medium being measured, in which case the mass of the adhering medium must follow with the oscillations, as compared with when the oscillatable unit is able to oscillate freely and without contact with the medium.

Piezoelectric elements change their dimensions (thickness, diameter), depending on a voltage difference applied in the direction of polarization. If an alternating voltage is applied, then the thickness oscillates: When the thickness increases, the diameter of the piezoelectric element decreases; when, on the other hand, the thickness decreases, then the diameter of the piezoelectric element correspondingly increases.

Because of this oscillatory behavior of the piezoelectric element, the voltage difference effects a flexing of the membrane 5 held in the housing. The oscillation tines of the oscillatable unit 2 arranged on the membrane 5 are caused by the oscillations of the membrane 5 to execute oscillations of opposite sense about their longitudinal axes. Oscillations of opposite sense have the advantage that the alternating forces exerted by each oscillation tine 3, 4 cancel one another. In this way, the mechanical loading of the membrane securement is minimized, so that essentially no oscillation energy is transferred to the housing.

The mechanical oscillation system formed of driver/receiver unit 6, membrane 5 and oscillatable unit 2 is a part of the oscillation circuit 7. In addition to the mechanical oscillation system, the oscillation circuit 7 also has an electrical component, which, for the most part, is embodied by the feedback electronics 9. The feedback electronics 9 can be constructed, for example, in the manner of the feedback electronics in the LIQUIPHANT M switch available from the assignee. The feedback electronics 9 provides periodic signals, especially rectangular signals, which are fed via the booster (amplifier circuit) to the driver/receiver unit 6 and, from there, transferred onto the membrane 5. This causes the membrane with the mounted, oscillatable unit 2, to oscillate with the predetermined frequency.

Also integrated into the oscillation circuit 7 is the microprocessor 8. This microprocessor 8 corrects, as an 'intelligent' member, the phase of the rectangular signals as a function of frequency. The phase correction value for each measured frequency value is stored in the memory unit 10. The phase correction value can still be influenced by other parameters, for example temperature. Therefore, a temperature sensor 13 is additionally provided, which delivers information concerning temperature at the measurement location, or in the region of the feedback electronics.

The input signal (In) fed to the microprocessor 8 is not converted A/D and subsequently filtered in the frequency domain, but, instead, is processed in the time domain. To this end, the microprocessor 8 executes the following steps:

In a first step, the rising edges of the rectangular input signal are used to determine the frequency of the oscillation circuit; in a second step, the phase correction value belonging to the determined frequency is ascertained; in a third step, an output signal is generated, which exhibits the corrected phase determined in the second step. This phase-corrected signal is amplified in the booster 12 and triggers the driver/receiver unit 6.

Potentially, the microprocessor also effects an amplitude correction, in addition to the phase correction. In this way, a weighting of the frequency occurs for the purpose of further 'intelligent' influencing of the signal. Additionally, it is provided that the (analog) feedback electronics 9 delivers to the microprocessor 8 a signal, which is amplitude-proportional to the input signal (In).

FIG. 2 shows graphically the behavior of phase and corrected phase as a function of frequency. The continuous curve with dots in it gives the phase as a function of frequency without phase correction by the microprocessor 8. The continuous curve with the x's characterizes the phase as a function of frequency in the case of phase adjustment by the microprocessor 8. In the illustrated case, the phase correction effects that the oscillations have a constant phase-frequency characteristic over the entire working range. In the illustrated case, a phase correction to 0° occurs.

Additionally, the microprocessor 8 effects an amplification of the output signals, with the amplification in the illustrated case likewise being controlled to a constant value in the working range.

The correction values for the phases as a function of frequency are, in an advantageous further development of the apparatus of the invention, available in the memory unit 10 in the form of a table or in the form of a function. Instead of the stored phase correction values, also an online determining of the optimal phase correction values matched to the actually existing conditions at the measurement location can occur. This is illustrated in FIG. 1 by the label (Ref.) and the dashed line. On the basis of a comparison of the phase of the input signal (In) and the phase of the output signal of the feedback electronics 9, it is possible to determine the present and, thus, optimal phase correction value. In this way, the reliability and accuracy of the apparatus of the invention can be increased still further.

The invention claimed is:

1. An apparatus for monitoring a predetermined fill level and/or for determining the density or viscosity of a medium in a container, comprising:

an oscillatable unit;

a driver/receiver unit;

feedback electronics;

a microprocessor; and an evaluation unit, wherein:

said oscillatable unit is placed according to one of the following: at the height of the predetermined fill level, or such that it reaches to a defined immersion depth into the medium;

said driver/receiver unit excites said oscillatable unit to oscillate with a predetermined oscillation frequency via said feedback electronics;

said evaluation unit detects the reaching of the predetermined fill level on the basis of a frequency change and/or an amplitude change of the oscillation of said oscillatable unit or determines the density or the viscosity of the medium on the basis of a change of the oscillation of the oscillatable unit, in said oscillation circuit, formed of said oscillatable unit and said feedback electronics;

said microprocessor corrects the phase of said feedback electronics over a predetermined frequency bandwidth in such a manner that the sum of the phases of said feedback electronics and said microprocessor follows a predetermined function f(v);

said feedback electronics provides said microprocessor with a periodic, rectangular, input signal, which is used by said microprocessor for determining a correction value for the phase;

said microprocessor evaluates and further processes the signal delivered from said feedback electronics in the time domain;

said microprocessor determines in a first step, on the basis of the edges of the rectangular input signal (In), the frequency of said oscillation circuit;

said microprocessor determines in a second step the phase correction value associated with the determined frequency; and said microprocessor issues an output signal with the corrected phase determined in the second step.

2. The apparatus as claimed in claim 1, wherein:
the frequency bandwidth preferably extends between the limits of 300 and 1500 Hz.

3. The apparatus as claimed in claim 1, wherein:
the sum of the phases of said feedback electronics and said microprocessor follow a predetermined function f(v) =constant.

4. The apparatus as claimed in claim 3, wherein:
associated with said microprocessor is a memory unit, in which at least one correction value is stored for the phase as a function of frequency.

5. The apparatus as claimed in claim 4, wherein:
said at least one correction value for the phase as a function of frequency is available in said memory unit in the form of a table or in the form of a computational algorithm.

6. The apparatus as claimed in claim 1, further comprising:
an input/display unit, via which the function f(v) can be prespecified.

7. The apparatus as claimed in claim 1, wherein:
said microprocessor determines the frequency over plural periods of the input signal (In) and performs a frequency weighting.

8. The apparatus as claimed in claim 1, further comprising:
an amplifier circuit, via which an output signal (Out) of said microprocessor is fed to said driver unit for said oscillatable unit.

9. The apparatus as claimed in claim 1, wherein:
said microprocessor additionally assumes the tasks of said evaluation unit and determines the reaching of the predetermined fill level or determines the viscosity or the density of the medium being measured.

10. The apparatus as claimed in claim 1, wherein:
said feedback electronics provides for said microprocessor a signal which is amplitude-proportional to the input signal (In).

11. The apparatus as claimed in claim 1, further comprising:
a further sensor, for measuring a process variable, said further sensor provides for the microprocessor information regarding the process variable, e.g. regarding the temperature, and wherein:
said microprocessor considers the influence of the process variable in providing a correction value for the phase.

* * * * *